(12) United States Patent
Dorn et al.

(10) Patent No.: US 10,596,020 B2
(45) Date of Patent: Mar. 24, 2020

(54) CATHETER DEVICE

(71) Applicant: Angiomed GmbH & Co. Medizintechnik KG, Karlsruhe (DE)

(72) Inventors: Jurgen Dorn, Neulussheim (DE); Martin Wuebbeling, Mannheim (DE)

(73) Assignee: Angiomed GmbH & Co. Medizintechnik KG, Karlsruhe (DE)

( * ) Notice: Subject to any disclaimer, the term of this patent is extended or adjusted under 35 U.S.C. 154(b) by 181 days.

(21) Appl. No.: 15/458,911

(22) Filed: Mar. 14, 2017

(65) Prior Publication Data

US 2017/0296369 A1    Oct. 19, 2017

Related U.S. Application Data

(60) Division of application No. 14/252,667, filed on Apr. 14, 2014, now Pat. No. 9,615,950, which is a continuation of application No. 11/917,499, filed as application No. PCT/EP2006/005805 on Jun. 16, 2006, now Pat. No. 8,758,420.

(51) Int. Cl.
*A61F 2/95*    (2013.01)
*A61F 2/966*    (2013.01)
(Continued)

(52) U.S. Cl.
CPC .............. *A61F 2/966* (2013.01); *A61F 2/95* (2013.01); *A61M 25/0108* (2013.01);
(Continued)

(58) Field of Classification Search
CPC .... A61F 2/95; A61F 2/966; A61F 2002/9522; A61F 2002/9517; A61F 2002/9583
See application file for complete search history.

(56) References Cited

U.S. PATENT DOCUMENTS 4,699,611 A * 10/1987 Bowden .................... A61F 2/04
                                                              604/105
5,275,622 A * 1/1994 Lazarus ................. A61B 17/11
                                                              604/103.02
(Continued)

FOREIGN PATENT DOCUMENTS

EP    0165963 A1    1/1986
EP    0611556 A1    8/1994
(Continued)

OTHER PUBLICATIONS

EP 06743169.2 filed Jun. 16, 2006 Office Action dated Apr. 20, 2011.
(Continued)

*Primary Examiner* — Seema Mathew
(74) *Attorney, Agent, or Firm* — Rutan & Tucker LLP (57) ABSTRACT

A catheter device having a shaft that extends from a proximal end to a distal end to carry on its distal end a self-expanding implant for intraluminal advance on a guidewire and delivery of the implant to an implant site by proximal withdrawal of a sheath that lies radially outside the implant in the catheter, the catheter including a first shaft element to pull the sheath proximally and a second shaft element to push the implant distally to prevent the implant moving proximally with the sheath when the sheath is pulled proximally, wherein the second shaft element carries a stopper for abutting the implant, the stopper including proximal and distal portions having different radiopacities.

17 Claims, 8 Drawing Sheets

(51) Int. Cl.
*A61M 25/01* (2006.01)
*A61F 2/958* (2013.01)

(52) U.S. Cl.
CPC . *A61M 25/0147* (2013.01); *A61F 2002/9517* (2013.01); *A61F 2002/9522* (2013.01); *A61F 2002/9583* (2013.01); *A61F 2250/0032* (2013.01); *A61F 2250/0098* (2013.01); *Y10T 29/49* (2015.01); *Y10T 29/49828* (2015.01)

(56) References Cited

U.S. PATENT DOCUMENTS

| | | | |
|---|---|---|---|
| 5,534,007 A * | 7/1996 | St. Germain | A61F 2/95 606/191 |
| 5,545,132 A | 8/1996 | Fagan et al. | |
| 5,649,908 A * | 7/1997 | Itoh | A61M 25/1006 604/103 |
| 5,651,786 A | 7/1997 | Abela et al. | |
| 5,741,429 A | 4/1998 | Donadio, III et al. | |
| 5,766,160 A | 6/1998 | Samson et al. | |
| 5,782,824 A | 7/1998 | Abela et al. | |
| 5,797,952 A | 8/1998 | Klein | |
| 5,833,694 A | 11/1998 | Poncet | |
| 5,843,027 A | 12/1998 | Stone et al. | |
| 5,876,376 A * | 3/1999 | Schwab | A61M 25/10 604/103 |
| 6,036,682 A | 3/2000 | Lange et al. | |
| 6,174,327 B1 * | 1/2001 | Mertens | A61F 2/958 606/108 |
| 6,210,434 B1 * | 4/2001 | Quiachon | A61B 17/11 623/1.11 |
| 6,241,758 B1 * | 6/2001 | Cox | A61F 2/95 606/108 |
| 6,285,903 B1 | 9/2001 | Rosenthal et al. | |
| 6,312,454 B1 | 11/2001 | Stockel et al. | |
| 7,232,452 B2 | 6/2007 | Adams et al. | |
| 7,955,384 B2 | 6/2011 | Rafiee et al. | |
| 8,252,015 B2 | 8/2012 | Leeflang et al. | |
| 8,323,326 B2 | 12/2012 | Dorn et al. | |
| 8,535,292 B2 | 9/2013 | Tollner et al. | |
| 8,758,420 B2 | 6/2014 | Dorn et al. | |
| 9,872,785 B2 | 1/2018 | Dorn et al. | |
| 2001/0027323 A1 | 10/2001 | Sullivan et al. | |
| 2003/0109886 A1 * | 6/2003 | Keegan | A61F 2/95 606/108 |
| 2004/0064179 A1 | 4/2004 | Linder et al. | |
| 2004/0193141 A1 | 9/2004 | Leopold et al. | |
| 2004/0193243 A1 | 9/2004 | Mangiardi et al. | |
| 2004/0199175 A1 | 10/2004 | Jaeger et al. | |
| 2004/0199240 A1 * | 10/2004 | Dorn | A61F 2/95 623/1.11 |
| 2004/0215331 A1 * | 10/2004 | Chew | A61F 2/88 623/1.21 |
| 2004/0220653 A1 | 11/2004 | Borg et al. | |
| 2004/0230286 A1 | 11/2004 | Moore et al. | |
| 2004/0267281 A1 * | 12/2004 | Harari | A61F 2/95 606/108 |
| 2005/0004553 A1 | 1/2005 | Douk | |
| 2005/0038493 A1 * | 2/2005 | Feeser | A61F 2/95 623/1.11 |
| 2005/0049682 A1 | 3/2005 | Leanna et al. | |
| 2005/0059957 A1 | 3/2005 | Campbell et al. | |
| 2005/0107737 A1 | 5/2005 | McDaniel | |
| 2005/0124917 A1 | 6/2005 | Skujins et al. | |
| 2006/0036307 A1 * | 2/2006 | Zarembo | A61N 1/056 607/122 |
| 2006/0052815 A1 | 3/2006 | Fitz et al. | |
| 2006/0184107 A1 | 8/2006 | Bencini et al. | |
| 2006/0212105 A1 * | 9/2006 | Dorn | A61F 2/95 623/1.11 |
| 2006/0216431 A1 | 9/2006 | Kerrigan | |
| 2006/0235502 A1 | 10/2006 | Belluche et al. | |
| 2006/0247661 A1 | 11/2006 | Richards et al. | |
| 2006/0263145 A1 | 11/2006 | Pal | |
| 2007/0005008 A1 | 1/2007 | Honebrink et al. | |
| 2007/0010878 A1 | 1/2007 | Rafiee et al. | |
| 2007/0270932 A1 * | 11/2007 | Headley | A61F 2/95 623/1.11 |
| 2007/0293930 A1 * | 12/2007 | Wang | A61F 2/91 623/1.11 |
| 2007/0299424 A1 | 12/2007 | Cumming et al. | |
| 2008/0021535 A1 | 1/2008 | Leopold et al. | |
| 2008/0091169 A1 | 4/2008 | Heideman et al. | |
| 2008/0114436 A1 | 5/2008 | Dieck et al. | |
| 2008/0234660 A2 | 9/2008 | Cumming et al. | |
| 2008/0300616 A1 | 12/2008 | Que et al. | |
| 2009/0093876 A1 * | 4/2009 | Nitzan | A61F 2/2433 623/2.11 |
| 2009/0204197 A1 | 8/2009 | Dorn et al. | |
| 2010/0087906 A1 | 4/2010 | Dorn et al. | |
| 2010/0145309 A1 | 6/2010 | Tollner et al. | |
| 2010/0145430 A1 | 6/2010 | Wubbeling et al. | |
| 2010/0249907 A1 | 9/2010 | Dorn et al. | |
| 2010/0286756 A1 | 11/2010 | Dorn et al. | |
| 2010/0314031 A1 | 12/2010 | Heideman et al. | |
| 2011/0184509 A1 | 7/2011 | Von Oepen et al. | |
| 2011/0196472 A1 * | 8/2011 | Sugimoto | A61F 2/95 623/1.12 |
| 2011/0208292 A1 | 8/2011 | Von Oepen et al. | |
| 2013/0304180 A1 * | 11/2013 | Green | A61F 2/966 623/1.11 |
| 2013/0304181 A1 * | 11/2013 | Green | A61F 2/966 623/1.11 |
| 2013/0340233 A1 | 12/2013 | Tollner et al. | |
| 2014/0025150 A1 * | 1/2014 | Lim | A61F 2/966 623/1.11 |
| 2016/0100965 A1 | 4/2016 | Nishigishi | |

FOREIGN PATENT DOCUMENTS

| | | |
|---|---|---|
| EP | 1095634 A2 | 5/2001 |
| EP | 1103281 A2 | 5/2001 |
| EP | 1890644 A1 | 2/2008 |
| GB | 453944 A | 9/1936 |
| JP | 07315147 A | 12/1995 |
| JP | 2002301161 A | 10/2002 |
| JP | 2004-530507 A | 10/2004 |
| JP | 2008-518687 A | 6/2008 |
| MX | 298767 | 5/2012 |
| WO | 1996039998 A2 | 12/1996 |
| WO | 2000041525 A2 | 7/2000 |
| WO | 2001034061 A1 | 5/2001 |
| WO | 2001056504 A1 | 8/2001 |
| WO | 2001087180 A2 | 11/2001 |
| WO | 2002015820 A2 | 2/2002 |
| WO | 2002045622 A2 | 6/2002 |
| WO | 2002087470 A1 | 11/2002 |
| WO | 2003002019 A2 | 1/2003 |
| WO | 2003002020 A2 | 1/2003 |
| WO | 2003003944 A2 | 1/2003 |
| WO | 2004062458 A2 | 7/2004 |
| WO | 2005053574 A2 | 6/2005 |
| WO | 2005072652 A1 | 8/2005 |
| WO | 2006050478 A1 | 5/2006 |
| WO | 2006113869 A2 | 10/2006 |
| WO | 2006113913 A2 | 10/2006 |
| WO | 2006133959 A1 | 12/2006 |
| WO | 2006133960 A1 | 12/2006 |
| WO | 2007004221 A1 | 1/2007 |
| WO | 2008031103 A2 | 3/2008 |

OTHER PUBLICATIONS

EP 06754410.6 filed Jun. 16, 2006 Office Action dated Aug. 18, 2010.

EP 07787316.4 filed Jul. 10, 2007 Office Action dated Dec. 23, 2011.

JP 2011-539027 filed May 27, 2011 Office Action dated Jan. 7, 2014.

JP 2011-539027 filed May 27, 2011 Office Action dated May 20, 2013.

(56) References Cited

OTHER PUBLICATIONS

PCT/EP2006/005805 filed Jun. 16, 2006 International Preliminary Report on Patentability dated Jun. 12, 2007.
PCT/EP2006/005805 filed Jun. 16, 2006 Search Report dated Oct. 20, 2006.
PCT/EP2006/005805 filed Jun. 16, 2006 Written Opinion dated Oct. 20, 2006.
PCT/EP2006/005806 filed Jun. 16, 2006 International Preliminary Report on Patentability dated Dec. 17, 2007.
PCT/EP2006/005806 filed Jun. 16, 2006 Search Report dated Sep. 27, 2006.
PCT/EP2006/005806 filed Jun. 16, 2006 Written Opinion dated Sep. 27, 2006.
PCT/EP2006/005807 filed Jun. 16, 2006 International Preliminary Report on Patentability dated Dec. 17, 2007.
PCT/EP2006/005807 filed Jun. 16, 2006 Search Report dated Sep. 27, 2006.
PCT/EP2006/005807 filed Jun. 16, 2006 Written Opinion dated Sep. 27, 2006.
PCT/EP2009/066313 filed Dec. 3, 2009 International Preliminary Report on Patentability dated Nov. 29, 2010.
PCT/EP2009/066313 filed Mar. 12, 2009 Search Report dated Mar. 25, 2010.
PCT/EP2009/066313 filed Mar. 12, 2009 Written Opinion dated Mar. 25, 2010.
PCT/EP2009/066314 filed Dec. 3, 2009 International Preliminary Report on Patentability dated Mar. 3, 2011.
PCT/EP2009/066314 filed Dec. 3, 2009 Search Report dated Mar. 5, 2010.
U.S. Appl. No. 11/917,303, filed Sep. 19, 2008 Notice of Allowance dated Aug. 10, 2012.
U.S. Appl. No. 11/917,431, filed Dec. 8, 2009 Final Office Action dated Oct. 23, 2013.
U.S. Appl. No. 11/917,431, filed Dec. 8, 2009 Non-Final Office Action dated Apr. 2, 2013.
U.S. Appl. No. 11/917,431, filed Dec. 8, 2009 Non-Final Office Action dated Mar. 6, 2012.
U.S. Appl. No. 11/917,499, filed Apr. 19, 2010 Non-Final Office Action dated Aug. 6, 2013.
U.S. Appl. No. 11/917,499, filed Apr. 19, 2010 Notice of Allowance dated Feb. 14, 2014.
U.S. Appl. No. 12/630,098, filed Dec. 3, 2009 Non-Final Office Action dated Apr. 4, 2012.
U.S. Appl. No. 12/630,156, filed Dec. 3, 2009 Advisory Action dated Mar. 30, 2012.
U.S. Appl. No. 12/630,156, filed Dec. 3, 2009 Final Office Action dated Feb. 14, 2013.
U.S. Appl. No. 12/630,156, filed Dec. 3, 2009 Final Office Action dated Jan. 6, 2012.
U.S. Appl. No. 12/630,156, filed Dec. 3, 2009 Non-Final Office Action dated Jul. 5, 2011.
U.S. Appl. No. 12/630,156, filed Dec. 3, 2009 Non-Final Office Action dated Sep. 7, 2012.
U.S. Appl. No. 12/630,156, filed Dec. 3, 2009 Notice of Allowance dated May 10, 2013.
U.S. Appl. No. 12/630,156, filed Dec. 3, 2009 Notice of Panel Decision dated May 17, 2012.
U.S. Appl. No. 13/975,119, filed Aug. 23, 2013 Advisory Office Action dated Sep. 4, 2014.
U.S. Appl. No. 13/975,119, filed Aug. 23, 2013 Final Office Action dated Jun. 11, 2014.
U.S. Appl. No. 13/975,119, filed Aug. 23, 2013 Non-Final Office Action dated Dec. 18, 2013.

\* cited by examiner

CATHETER DEVICE

PRIORITY

This application is a division of U.S. patent application Ser. No. 14/252,667, filed Apr. 14, 2014, now U.S. Pat. No. 9,615,950, which is a continuation of U.S. patent application Ser. No. 11/917,499, filed Apr. 19, 2010, now U.S. Pat. No. 8,758,420, which is a 35 U.S.C. § 371 application of International Application No. PCT/EP2006/005805, filed Jun. 16, 2006, which claims priority to GB 0512319.5, filed Jun. 16, 2005, the entireties of which are hereby incorporated by reference.

FIELD OF THE INVENTION

This invention relates to a catheter device having a shaft, a rapid-exchange guidewire lumen (one which terminates at a proximal guidewire exit port that is distal of the proximal end of the catheter) and a distal end which exhibits a sheath which can be withdrawn proximally to release a self-expanding implant such as a stent. To prevent the self-expanding stent moving proximally with the proximally-moving sheath, the catheter device includes a stopper which bears on the stent and resists its proximal movement.

BACKGROUND

Conventionally, such a catheter device exhibits a shaft comprising an outer tube connected to the sheath and an inner shaft connected to the stopper, whereby the proximal movement of the sheath is accomplished by imposing an endwise tension on the outer tube, with the inner shaft carrying an endwise compression stress, as the stopper at the distal end of the inner shaft works to resist proximal movement of the stent. For examples, see WO 2003/003944, WO 2003/002020, WO 2004/062458 and EP 1095634.

Such conventional systems can work well, and can be of relatively simple construction. However, the present inventor has discovered that they are nevertheless capable of improvement.

One disadvantage noted by the present inventor is that release of the stent requires the medical practitioner to maintain the inner pusher shaft unchanged in axial disposition relative to the site of stenting in the body of the patient, while pulling back on the outer tube of the shaft to release the stent. This pulling back of the outer tube requires relative movement of the outer tube in the bodily lumen (or guide catheter) in which it has been advanced to the site of stenting. Any friction or resistance to axial movement of the outer tube in the lumen in which it is located hinders the objective of maintaining the stopper in a precise disposition relative to the target stenting site. In practice, it is customary to compensate for axial strain in known systems by positioning the stent slightly distal of the desired end position before commencing stent deployment by pulling back the sleeve. The present invention is useful in reducing or eliminating the need for such compensation.

SUMMARY

The present invention is an improvement of the invention disclosed in WO 2005/053574.

It is an object of the present invention to improve the visualization capabilities of the catheter-based implant delivery system to a target implant site in a human or animal body. These visualization capabilities are particularly important, when the implant is intraluminally advanced along a tortuous path through the system of body vessels, and the medical practitioner needs to ascertain the exact position of the implant. It is another object of the present invention to improve the capability of the delivery system to accurately release the implant at the implant site by proximal withdrawal of the sheath radially surrounding the implant.

Another object of the invention is to enable one catheter delivery system to deliver to an implant site a range of implants of different lengths.

These objects are solved by the feature combinations of the independent claims below. Preferred, or optional features are subject of dependent claims.

In accordance with one aspect of the present invention, a catheter device is provided in which a second shaft element for pushing the implant distally to prevent the implant from moving proximally with a sheath constraining the implant in a radially compressed delivery configuration inside the sheath of the catheter device carries a stopper for abutting the implant. The stopper according to the present invention comprises proximal and distal portions having different radiopacities. As the implant abuts the stopper during proximal withdrawal of the surrounding sheath, visualization of the position of the stopper, and hence of the implant, is facilitated if the stopper exhibits at its distal and proximal ends different radiopacities which give rise to a contrast on the X-ray image the medical practitioner is viewing when trying to ascertain the position of the implant inside the body vessel. Moreover, visualizing the position of the implant by means of the stopper has the advantage that a component of the catheter device itself is used for the visualization which is not to be crimped down to a reduced diameter profile for delivery, as it is the case when the implant were to be furnished with improved visualization capabilities.

Preferably, the distal portion of the stopper is made of a material that is nonradiopaque. Due to the implant being made of a metal, the contrast is further enhanced. In a preferred embodiment of the invention, the proximal portion of the stopper is made of stainless steel which can easily be welded to the second shaft element of the catheter device. Preferably, the distal portion of the stopper is made of a polymer with high axial stiffness, preferably PEEK. One can look upon this distal portion as a spacer, between the proximal portion that does the stopping work and the implant that has to be stopped. The distal portion has a distal-facing abutment surface that abuts the implant and a proximal-facing abutment surface that abuts the stopper proximal portion.

It will be gathered that a single catheter system in this way acquires a capability to delivery implants in a range of implant lengths, simply choosing a length of the stopper distal portion complementary to the chosen implant length, so that the aggregate length of the implant and distal stopper portion remains more or less unchanged.

In accordance with the disclosure of WO 2005/053574, the present invention is useful in improving positional placement of a self-expanding stent at a target stenting site in a human or animal body, when using a transluminal, catheter-based stent delivery system. A catheter device of the type identified above is provided, and in which the shaft of the catheter device features a shaft pusher tube with a lumen and with a distal end operatively connected to the stent stopper, the lumen of the pusher tube being occupied by a pull wire or rod which is arranged to pull back the sheath surrounding the self-expanding stent. The wire or rod can itself be tubular. It is resistant to endwise extension of its length, and the pusher tube is resistant to endwise shortening of length when placed in endwise compression. Normally, both so-axial elements will be of a suitable metal such as stainless steel.

The present invention can be useful in a method of deploying a self-expanding stent in which a sheath surrounding the stent is pulled back proximally by a pull wire within the shaft of a rapid-exchange transluminal catheter delivery system for the stent.

It will be appreciated that, with an arrangement in accordance with the present invention, there is no requirement for any axial movement of the outer shaft tube relative to the lumen in which it slides. The lumen could be that of a human or animal body, or that of a catheter such as a guide catheter, lying within such a bodily lumen. Instead, since the shaft tube is connected to the stent stopper, it is required that there be no such axial movement during release of the prosthesis. Accordingly, any binding between the shaft tube and any surrounding guide catheter, or bodily tissue of the access lumen, and any friction acting on the outside surface of the shaft tube, is turned by the present invention into an advantage rather than a problem, because it will help to confirm the axial position of the shaft tube relative to the stopper and the stenting site. The more tortuous the access lumen in the body, the more likely it is that during release of the stent there will be no axial movement of the shaft tube and stopper relative to the intended stenting site.

Furthermore, a shaft tube has more inherent resistance to elastic axial compression or other end-to-end shortening than a mere wire within the lumen of the tube. Thus, regardless how great are the tensile stresses imposed on the pull wire during the push-pull activity of stent release, there should be less unwanted proximal movement of the stopper from the intended site of stenting. The shaft tube may be of stainless steel or of a cobalt/chromium/nickel alloy sold under the trademark PHYNOX.

Furthermore, the sheath itself can also be metal-reinforced (such as by an embedded metal braid) and so also with a high capacity to resist axial strain, increasing the precision with which the operator of the catheter device can control the progressive withdrawal of the sheath and release of the stent. Many doctors prefer to release a self-expanding stent in a step-wise movement. If the pulling system stretches, then a step-wise movement can have the consequence of a time-dependent response at the distal end of the system, and a relaxation of the pulling system between successive pulling steps, with consequent undesirable reverse distal movement of the sheath or else "lost movement" in the pulling system as it once again strains to take up the pull tension with successive step-wise pulls at the proximal end of the system.

Thus, the shaft tube is conveniently a stainless steel or PHYNOX hypotube and the pull wire is conveniently of metal, such as a stainless steel wire, either solid or hollow. While the sheath will very likely be of polymer, it can be made resistant to elastic stretching during proximal withdrawal and release of the stent by embedding within the annular wall thickness of the polymer sheath a fiber reinforcement such as a braided metal mesh. Here, there is effectively a continuous strand of elastic strain-resistant metal in the pulling system, all the way from the proximal end of the pull wire to the distal end of the polymer sheath, again adding to the precision of proximal withdrawal, and minimizing any elastic strain within the system during withdrawal.

The pull wire can be connected to the sheath by, for example, first and second metal rings, one inside the other, and sandwiching the sheath so that one of the metal rings is inside the sheath annulus and the other is outside the sheath annulus. The inside metal ring would normally be welded, soldered or brazed to the distal end of the pull wire (adhesives being generally disfavored in failure-critical applications in such stent delivery devices) while the outer metal ring can be swaged down onto the sheath to press the sheath radially inwardly to a radius less than that of the outer diameter of the inside metal ring.

The present applicant has developed stent delivery systems (see WO 2001/34061) which feature a catheter system having a heat-formed tapered distal tip which can help to reduce trauma to the body as the catheter system is advanced in a bodily lumen along its guidewire. Preferably the sheath has a tapered distal tip, which can be heat-formed, and which desirably tapers down to an end orifice which fits relatively closely around the cylindrical outside surface of the guidewire.

The catheter shaft diameter may be defined by the pusher tube, and is smaller than the diameter of the sheath around the stent. At the proximal end of the sheath, it may be attractive to taper the diameter down to a relatively snug fit around the outside of the shaft tube (but not so snug as to resist proximal axial sliding of the sheath along the outside of the shaft tube). It is contemplated to create the proximal guidewire exit port in the tapered proximal end of such a formed sheath, as explained below in more detail in relation to the accompanying drawings.

The proximal end of the sheath can be joined to a metal collar that defines a proximal guidewire exit port lumen and another lumen to slidably receive the outer tube of the catheter shaft. The collar can be given a domed shape facing proximally, to facilitate atraumatic withdrawal of the catheter system.

One way of connecting the shaft tube to the stopper is by way of a pusher-guider tube which defines a guidewire lumen and carries the stopper at a location near the distal end of the pusher-guider tube, or at its distal end. The proximal end of the pusher-guider tube is arranged to one side of the distal end of the shaft tube and fixed relative to it, such as by welding or glueing. Conveniently, both the pusher-guider tube and the shaft tube are of metal such as stainless steel, simplifying the task of bonding together side-by-side the proximal end of the pusher tube and the distal end of the shaft tube, as by welding or brazing. Other means of joining these tube sections will be apparent to those readers skilled in the field, who will also appreciate that adhesive compositions are generally disfavored, whenever failure of the adhesive bond results in failure of the device and risk to the patient, in use.

Distal of the stopper, the pusher-guider tube is not required to carry any substantial axial compressive stress. In any event, it should be soft and easily bendable so as to keep the catheter tip as floppy as possible. The compression resistant pusher-guider tube could be extended distally beyond the stopper, all the way to the distal end of the sheath, in order to define a guidewire lumen which extends within the pusher tube all the way to the distal end of the system. Indeed, the pusher tube could extend into an atraumatic tip distal of the distal end of the sheath. In this way, the tapered tip of the sheath could be omitted.

Thus, there can be provided, distal of the stopper, a pusher tube extension, which continues the guidewire lumen from the stopper to the distal end of the system, but which may be of less heavy construction, being formed for example of thin wall polymer tube. Another useful purpose of such a guidewire lumen distal of the stopper is for carrying a radiopaque marker band to indicate the distal end of the stent within the delivery system, so that the radiologist can determine with precision where the stent in the delivery system is located relative to the target stenting site.

For the sake of completeness, and to put the present invention in the context of the prior art documents seen with hindsight to be helpful in appreciating how the present invention contributes to the state of the art, reference will now be made to EP 611556 and WO 1996/039998. EP 611556 discloses a rapid exchange balloon catheter stent delivery system in which a sheath is pulled back proximally by a pull wire, to expose a stent mounted on a balloon, so that the stent can then be deployed by inflation of the balloon. The stent is not a self-expanding stent, so is not pressing on the luminal surface of the sheath during advance of the delivery system to bring the stent into the location of stenting. Accordingly, the balloon-expandable stent is not liable to be carried proximally by the sheath when the sheath is pulled proximally. Accordingly, there is no need for a stopper to resist unwanted proximal movement of the stent. Accordingly, there is no significant resistance to proximal movement of the sheath. Accordingly, there is no need for the shaft of the system, defining the lumen in which the pull wire is located, to be resistant to axial compressive stresses. The problem of designing a system to deliver a self-expanding stent which maintains the axial position of the stent correct during stepwise release of the stent is not a problem experienced with balloon-expandable stent delivery systems.

Conversely, WO 1996/039998 is a disclosure which is concerned with systems which will resist endwise compression during delivery of a self-expanding stent and proximal withdrawal of a sheath surrounding such a stent. The problem is addressed by providing within the delivery system an inner core which is resistant to endwise compression, and providing a stopper near the distal end of the inner core. Thus, the pull wire is not housed within the lumen of the element that is in endwise compression during stent release but instead, is lying side-by-side with the element that is subject to endwise compression. Any capability that the outer sheath of the system might have to carry endwise compression stress remains unutilized.

For a better understanding of the present invention, and to show more clearly how the same may be carried into effect, reference will now be made, by way of example, to the accompanying drawings.

DETAILED DESCRIPTION

Figure 1:
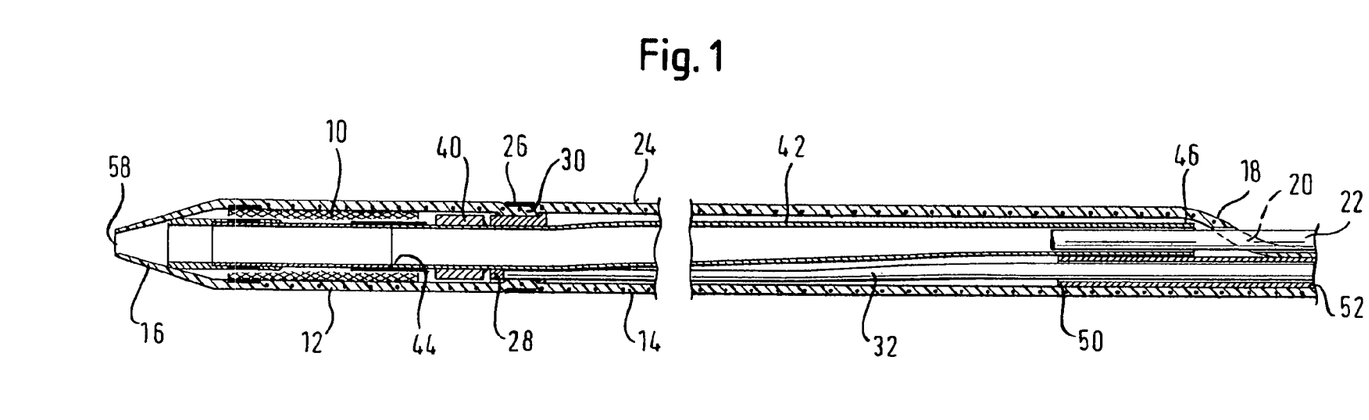
FIG. 1 is a longitudinal diametrical section through the distal end zone of a catheter device.
Figure 2:
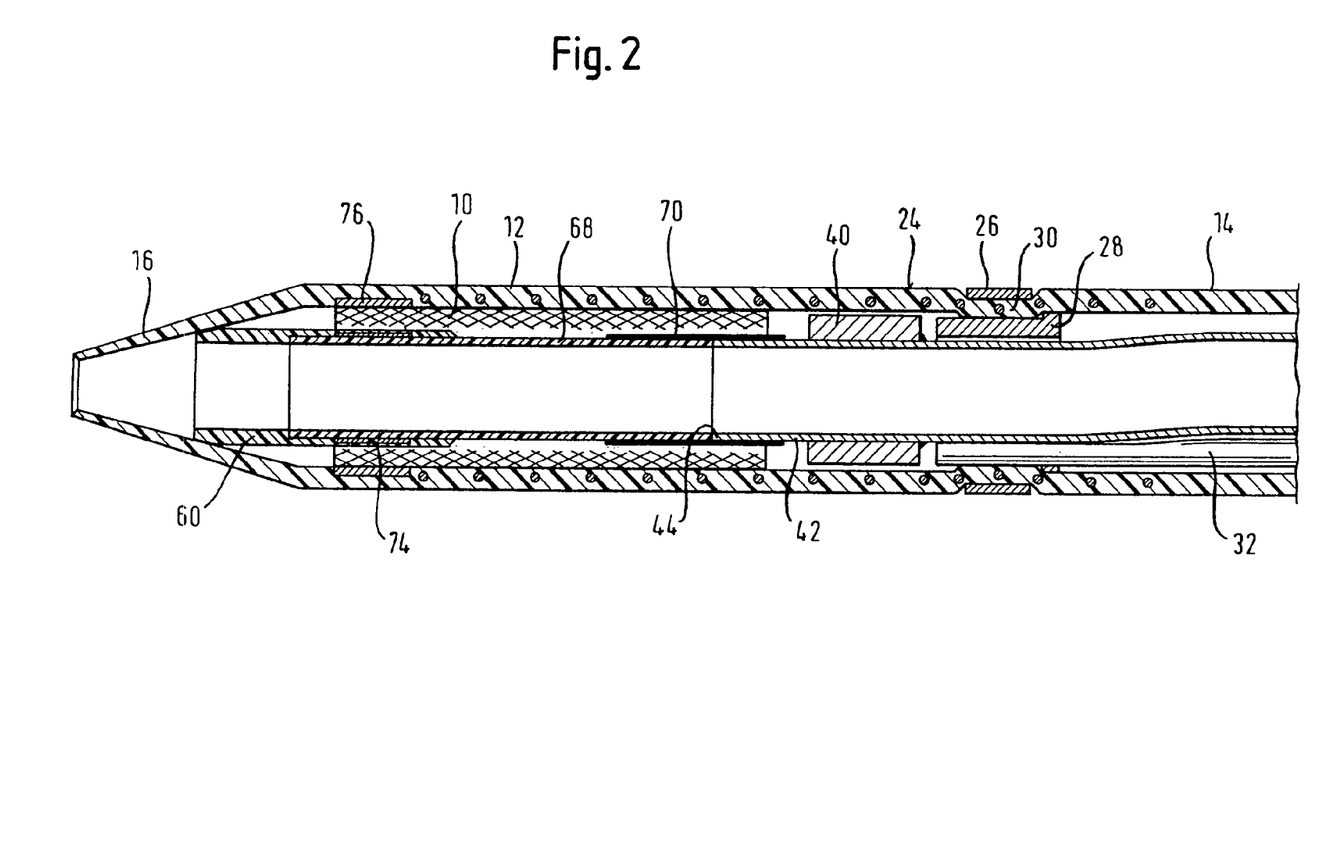
FIG. 2 is the identical section, at larger scale, through the distal part of the distal zone of FIG. 1.
Figure 3:
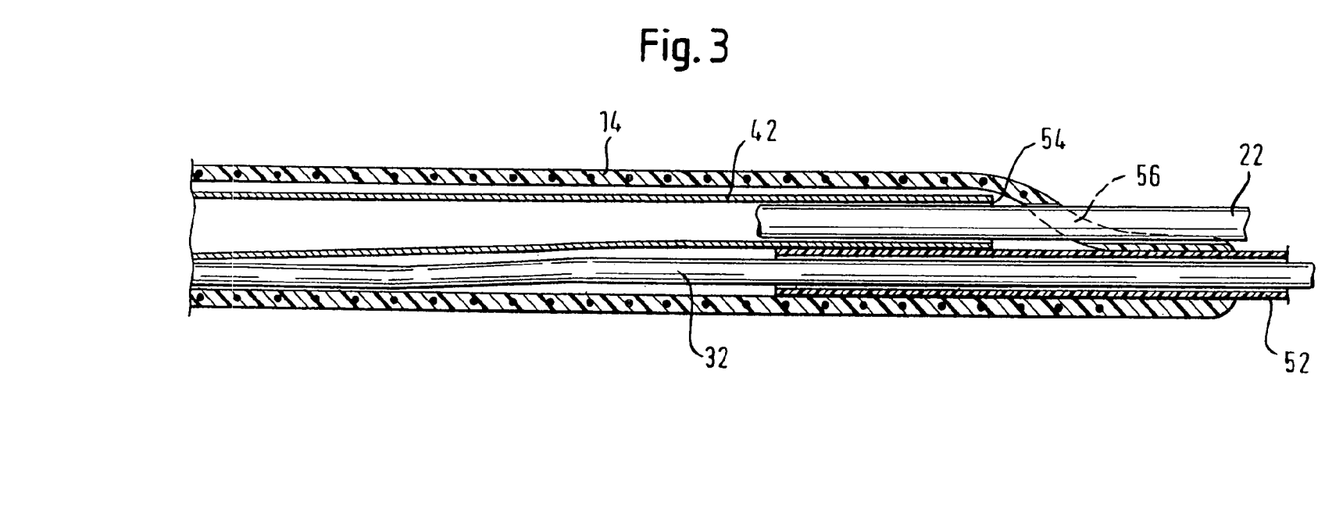
FIG. 3 is an identical section, at larger scale, through the proximal part of the distal zone of FIG. 1.

Referring to FIGS. 1, 2 and 3 which form part of the invention described in WO-A-2005/053574, a self-expanding stent 10, or stent graft, lies inside the distal end zone 12 of a sheath 14 with a tapered distal tip 16 and a heat-formed proximal end 18 which defines the orifice 20 of a proximal guidewire exit port for a guidewire 22. Being a self-expander, the stent 10 is, at least at body temperature, putting compressive stress on the luminal surface of the sleeve 14 in the distal end zone 12. Proximal of the stent 10, and on the abluminal surface 24 of the sleeve 14, is a swaged marker band 26 of radiopaque metallic material, which is pressing radially inwardly the material of the sheath 14 within the band 26. Radially inside the sheath at this point is a stepped metal annulus 28 which is itself put under radially inwardly compressive stress by the material 30 of the sheath 14 inside the marker band 26. Thus, the sheath material 30 is compressed between metal bands inside (28) and outside (26) the sheath 14. Brazed to the annulus 28 is a pull wire 32 which runs from the annulus 28 all the way back to the proximal end of the catheter device, whereby endwise tensile stress imposed on the proximal end of the pull wire 32 will pull proximally the annulus 28 and thereby impose on portions of the sheath 14 distal of the annulus 28 an endwise tensile stress, for pulling the sheath 14 proximally with respect to the stent, to release the stent. At the same time, portions of the sheath 14 proximal of the annulus 28 will be pushed proximally.

A pusher annulus 40 is located in the lumen of the sheath 14 just proximal of the stent 10. Its purpose is to resist proximal movement of the stent 10, when the sheath 14 is withdrawn proximally from the stent 10. It can also serve as a radiopaque marker band to indicate the proximal end of the stent 10. The pusher annulus 40 is brazed or welded or otherwise fixed to a pusher-guider tube 42 which is conveniently of stainless steel or PHYNOX and which has its distal end 44 distal of the pusher annulus 40 and within the lumen of the stent 10. The proximal end 46 of the pusher tube 42 is arranged side-by-side with the distal end 50 of a shaft pusher tube 52 of the catheter device which extends all the way to the proximal end of the catheter device and is conveniently provided as a PHYNOX or stainless steel hypo tube. The lumen of this shaft tube 52 carries the pull wire 32. The overlapping portions 46 and 50 of the pusher-guider tube and shaft pusher tube are bonded to each other, conveniently by brazing, so that they effectively form a single metal strand from the proximal end of the catheter device to the stent pusher annulus 40. As can be seen in FIG. 1 and FIG. 3, the end orifice 54 of the pusher tube 42 is co-linear with the orifice 56 in the heat-formed end 18 of the sheath 14, which defines the proximal guidewire exit lumen. Thus, when a guidewire 22 is advanced through the guidewire lumen of the catheter device by introducing it into the end orifice 58 of the tapered distal tip 16 of the sheath 14, the end of the guidewire will advance proximally along the pusher tube and exit through the port 56.

Figure 2A:
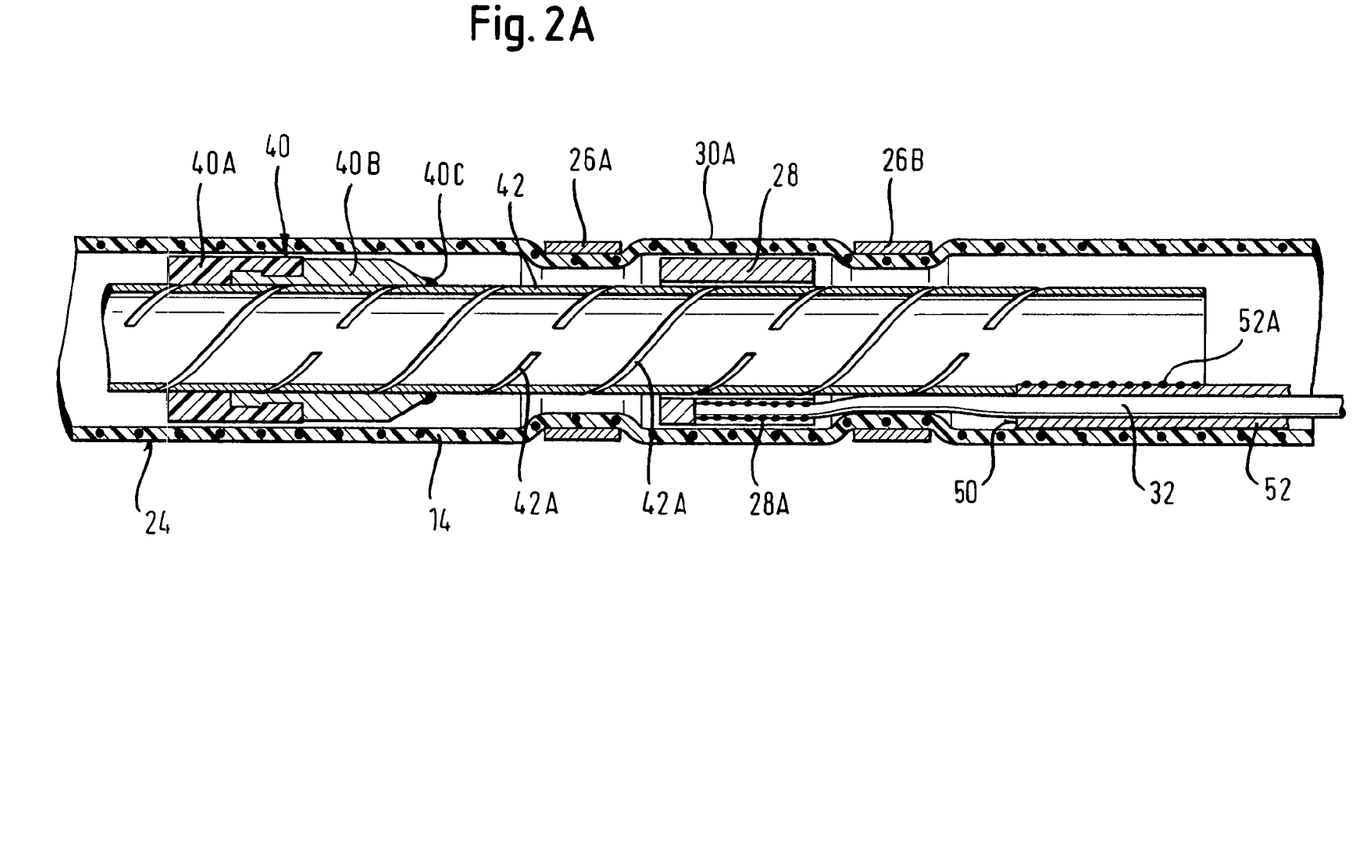
FIG. 2A is a section, at a larger scale, through a distal part of a distal zone of a catheter device according to the present invention.

Now to be described is a particular embodiment of the present invention in FIG. 2A which is an improvement of the invention described in WO 2005/053574 (WO '574). It is obvious for the skilled person that parts of the disclosure of WO '574 also apply to what is shown in FIG. 2A.

With reference to FIG. 2A, proximal of the stent (not shown), and on the abluminal surface 24 of the sleeve 14, are swaged steel bands 26A, 26B, which are pressing the material of the sheath 14 enclosed by the bands 26A, 26B radially inwardly. Radially inside the sheath and longitudinally between the two bands 26a, 26b is a metal annulus 28. The metal annulus 28 is welded to a pull wire 32. The location at which the annulus 28 is welded to the pull wire 32 is indicated by reference numeral 28A. As can be seen in FIG. 2A, the diameter of the pull wire 32 is slightly reduced in a portion that lies radially inside the steel band 26B in order to accommodate the reduced inner diameter portion of the sheath 14. The outer diameter of the steel bands 26A, 26B is either equal or greater than the outer diameter of the sheath 14. The steel bands 26A, 26B are swaged onto the material of the sheath 14, but other methods of fixing the steel bands to the sheath are contemplated as well, such as gluing, crimping etc.

The bands 26a, 26b may not necessarily be made of stainless steel. Other materials include polymers, such as PHYNOX™, titanium, shape memory alloys, such as NITINO™. The use of NITINO™ may be advantageous in that the crimping down of the sheath to a reduced diameter at the position of the bands may occur upon exposing the catheter to a temperature change, such as by inserting it into the body of a human or an animal. The bands may also be made of radiopaque material so as to serve as marker bands. It is conceivable that the reduced inner diameter portion proximal of the annulus 28 may be provided by a tube heat-shrunk onto the luminal surface 24 of the sheath 14 at the location of the steel band 26B in order to effect reduction of the inner diameter of the sheath.

The inventors of the present invention have discovered that reducing the inner diameter of the sheath 14 proximal of the annulus 28 is advantageous in that the sheath remains freely rotatable with respect to the inner structure of the delivery system that effects proximal withdrawal of the sheath. Furthermore, the tensile strength of the sheath in the proximity of the annulus 28 remains unchanged due to the constant wall thickness of the catheter sheath in the proximity of the annulus 28.

It is to be noted that, upon proximal movement of the annulus 28 due to pulling the shaft tube in proximal direction, the annulus 28 abuts the reduced inner diameter portion of the sheath 14 at the position of the steel band 26B, thus effecting proximal withdrawal of the sheath 14 to release the stent at the distal end portion of the sheath 14.

Furthermore, it is conceivable to provide an annular band, or other means, on the luminal surface of the sheath 14 proximal of the annulus which restricts proximal movement of the annulus upon pulling action on the pull wire 32.

A second steel band 26A is provided distally of the annulus 28 on the abluminal surface 24 of the sheath 14. This steel band 26A takes up the push forces during advancement of the catheter device to the stenting site. The same considerations apply to the steel band 26A, as previously described with respect to the steel band 26B.

In any event, any of the above described means for reducing the inner diameter of the sheath proximal of the annulus 28 must withstand the proximally directed forces when the annulus abuts on the reduced diameter portion when pulling proximally on the pull wire 32, and thus the sheath 14.

FIG. 2A further depicts a pusher-guider tube 42 which is arranged side-by-side with the distal end 50 of the pusher tube 52 of the catheter device which extends all the way to the proximal end of the catheter device. The pusher tube 52 is conveniently provided as a PHYNOX™ or stainless steel hypotube.

As shown in FIG. 2A, the pusher-guider tube 42, in a portion of its length between its distal end (not shown) and its portion at which the pusher-guider tube 42 is arranged side-by-side with the distal end 50 of the shaft pusher tube 52 exhibits slits through the wall thickness of the pusher-guider tube 42. These slits are preferably arranged in a helical string along the axial length of the pusher-guider tube 42. They are discontinuous so that, typically, each slit in the string extends approximately two complete turns around the longitudinal axis of the pusher-guider tube 42. The portions of solid material, between each two adjacent spiral cuts in the helical string, impart the pusher-guider tube 42 with sufficient torqueability in both senses of rotation of one end of the pusher-guider tube relative to its other end.

These spiral cuts are preferably made by a laser, but other methods for cutting the slits are conceivable, such as erosion cutting etc.

Of course, the cuts can be arranged on the outer surface, and through the wall thickness of the pusher tube, in other patterns, such as a sinusoidal pattern, helical pattern with varying pitch, circumferentially offset double or multiple helical or sinusoidal patterns, a pattern of cuts with finite length in which the cuts extend perpendicular, or slightly inclined to the long axis of the pusher-guider tube and in which axially adjacent cuts are circumferentially offset, etc. The spiral cut arrangement may be a double- or multi-helix design in which at least the second helix is circumferentially offset by 180° relative to the first helix.

Any pattern is conceivable which maintains sufficient axial stability or is able to accommodate compressive forces along the long axis of the pusher-guider tube 42 and yet renders the pusher-guider tube 42 sufficiently axially elastic or bendable, yet with enough torqueability.

The skilled person may select such slit patterns from stent designs that exhibit good axial elasticity and bendability, sufficient endwise compression resistance and sufficient torqueability. The axial elasticity properties of the stent, or any other implant to be delivered by the catheter-based delivery system of the present invention, are not the same as those required in the pusher-guider tube.

Preferably, the width of the laser cut slits and the selected pitch design is such that axial deflection of the pusher-guider tube 42 is effected with minimal or virtually zero amount of force. The wall thickness of the pusher-guider tube 42 is preferably selected such that the radiopacity of the stent is not compromised. For that reason the wall thickness of the pusher-guider tube 42 is substantially less than the wall thickness of the tubular stent to be delivered by the catheter-based delivery system.

The inner diameter of the pusher-guider tube 42 is typically at least 1.0 mm, and the outer diameter is typically 1.1 mm or more. The inner diameter and the outer diameter of the pusher guider-tube 42 is selected such to provide, on the one hand, a sufficient gap between a guide wire extending through the lumen of the pusher-guider tube 42, thus reducing the likelihood of adhesion of the guide wire to the luminal surface of the pusher-guider tube 42, and, on the other hand, a sufficient gap between the abluminal surface of the pusher-guider tube 42 and the luminal surface of the stent.

It is even conceivable, instead of cutting slits through the wall thickness of the pusher-guider tube 42, to provide apertures of any shape and size other than a slit in the wall of the pusher-guider tube 42, so long as the pusher-guider tube 42 exhibits the above-mentioned properties.

The above mentioned properties may even be achieved by changing the composition of the material used for the pusher-guider tube 42 along its length. Moreover, the pusher-guider tube 42 may be made of a thin-walled stainless steel tube, or a stainless steel hypotube, which has been exposed to a thermal treatment process such to exhibit a 40% elongation at fracture, or greater at body temperature.

For achieving the above described properties, the pusher-guider tube 42 may be made of a thin-walled stainless steel tube that is fully or partially annealed. It is preferred that the annealing of various portions along the axial length of the pusher-guider tube 42 is such that the resistance of the portion radially inside the stent to bending is less than the bending flexibility of the stent itself. Either a thin-walled stainless steel tube fully annealed to exhibit a 40% elongation at fracture, or greater at body temperature, or a thin-walled stainless steel tube fully or partially annealed and comprising non-continuous spiral cuts with varying pitch, or a thin-walled stainless steel tube not being annealed and having non-continuous spiral cuts with varying pitch, may be used for the pusher-guider tube 42.

The pusher-guider tube 42 can have different lengths. Although not shown in FIG. 2A, the pusher-guider tube 42 may extend beyond the distal end of the stent, or it can terminate at the stopper 40 for abutting the stent, as described below, and connected to a polymer tubing distally of the stopper 40. The connection may be established by various means, such as heat-shrinking a sleeve over the connecting portion, overmolding, gluing, etc.

The pusher annulus 40, as shown in FIG. 2A, comprises two parts. However, it is conceivable that it may comprise more than two parts. The proximal part 40B is made of metal, preferably stainless steel, such as 1.4301 or 1.4305 stainless steel, and is welded at its proximal chamfered end to the pusher-guider tube 42, as indicated by reference numeral 40C. However, the proximal metal part may be alternatively glued to the pusher-guider tube 42. The distal part 40A of the pusher annulus 40 is made of a polymer which is stiff enough to withstand the forces exerted by the abutting stent when proximally withdrawing the outer sheath 14. The polymer part 40A can be seen as a spacer. It is preferably overmolded to the steel part 40B, however, other ways of connecting the polymer part 40A to the metal part 40B are conceivable.

As shown in FIG. 2A, a mechanical inter-engagement interference fit is provided at the abutting portion of the polymer part 40A and the metal part 40B. The recessed portions of the polymer part 40A and the metal part 40B are not restricted to the shape as shown in FIG. 2A. Other interference fit designs are conceivable so long as dislodging of the polymer part 40A from the metal part 40B is prevented.

The polymer part 40A has preferably a length equal to or greater than 2 mm. The polymer part 40A due to its non-radiopacity gives good contrast to the metal stent when monitoring the advancement of the catheter-based delivery system to the stenting site by x-ray monitoring equipment.

It is also conceivable that the polymer part 40A may have different lengths in order for the same delivery system to accommodate different lengths of stents.

The heterogeneous radiopacity helps in making the stent visible during intraluminal advancement, that is to say to provide a medium adjacent the stent that has a radiopacity which is different to that of the stent, and thus helps in imaging the stent and identifying the position of the proximal end of the stent during intraluminal delivery.

Figure 4:
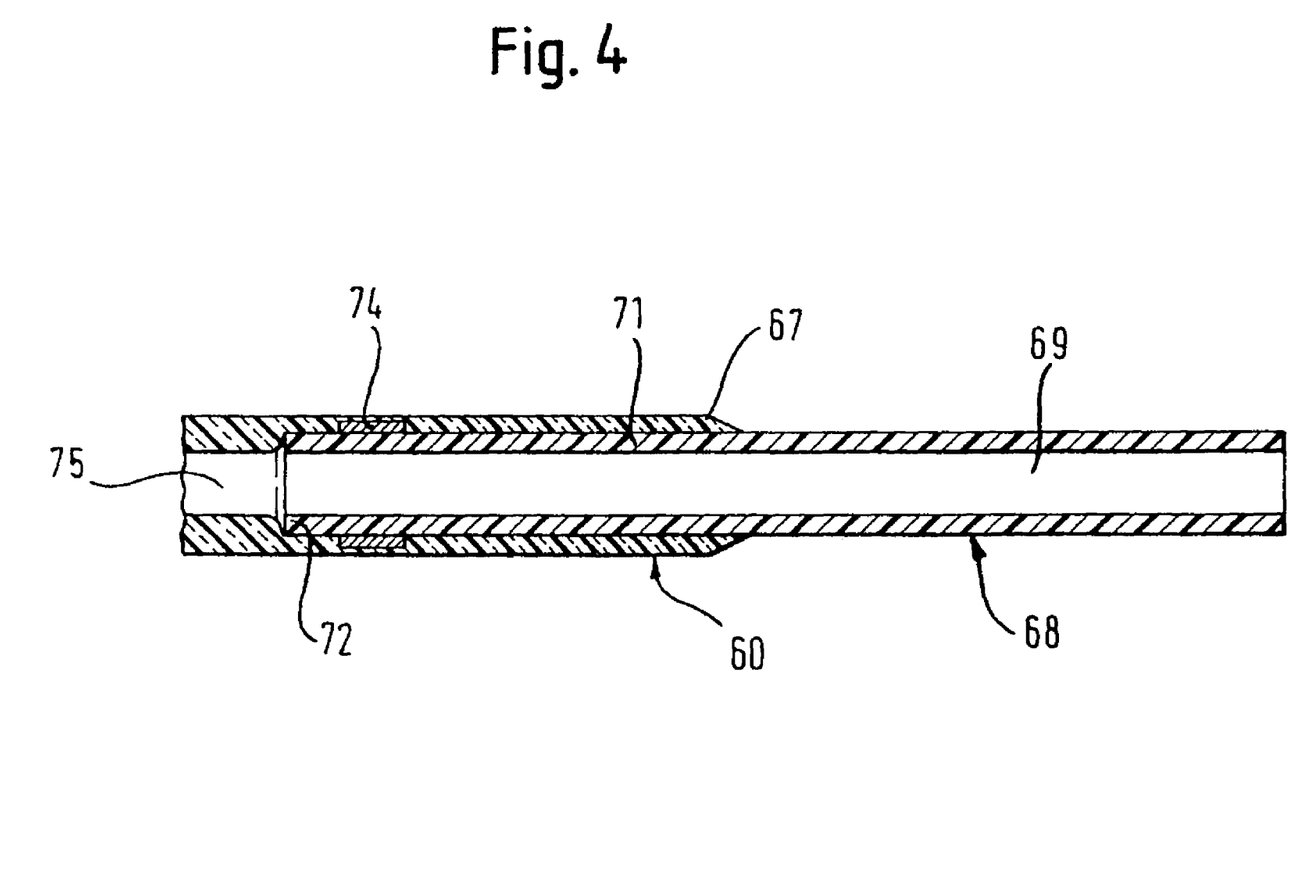
FIG. 4 is a longitudinal diametrical section, at enlarged scale, of the junction between the pusher tube and pusher tube extension of FIG. 1.

With reference to FIG. 2 and FIG. 4, we will now explain the structure of the pusher tube extension, distal of the pusher annulus 40, and located between that annulus and the end orifice 58 at the distal end of the sheath 14.

The metal pusher tube 42 extends for a short distance distally of the pusher annulus 40. A distal extension inner catheter 68 of polyimide abuts the distal end of the pusher tube 42 and is secured to that pusher tube by a shrink tube 70 radially overlying the distal end of the pusher tube 42 and the proximal end of the inner catheter 68. This shrink tube 70 is of PET (which shrinks radially downward to grip both these abutting portions).

FIG. 4 shows the distal end 72 of the distal extension inner catheter tube 68 and a bore 69 within it, open to the distal end of the inner catheter 68, and terminating proximally at an end-to-end butt joint with the distal end of the metal pusher tube 42. A tip extension catheter 60 of PEBA polymer (PEBAX®) receives the distal end 72 of the inner catheter 68, so that its proximal end 67 overlaps the abluminal wall of the catheter 68. Around the distal end 72 of the catheter 68, and sandwiched between the distal catheter 68 and the proximal end zone of the tip catheter 60, is a second radiopaque metal marker band 74, and the whole assembly is bonded together with a cyanoacrylate adhesive composition. The PEBAX tip extension catheter 60 extends into the tapered lumen of the taper 16 of the distal end of the sheath 14. Of note is that the bore 75 of the catheter 60 is contiguous and smooth with the bore 69 of the catheter 68 for smooth progress of a guidewire. Catheter 60 is soft and floppy but has a larger outside diameter than catheter 68, which helps to ease the end orifice of the sheath 14 open when it begins to withdraw. Proximal end 67 of catheter 60 is tapered inwardly. This is because, should a physician decide to sheath the distal end of the delivery system after stent deployment by re-advancing the sheath distally, the tapered tip 16 of the sheath is required to advance distally back onto the abluminal surface of catheter 60 and the taper 67 helps that advance.

Reverting to FIG. 2, fixed to the lumen surface of the sheath 14, just proximal of the tapered tip zone 16, is a third radiopaque metal marker band 76 and it will be seen that this marker band lies radially outside the second marker band 74 within the distal extension inner catheter 68.

To deploy the stent the pull wire is pulled by an actuator at the proximal end of the system. A suitable actuator is described below, as part of a catheter-based delivery system illustrated herein.

In use, the distal end zone of the catheter system, as shown in the drawings, is advanced along a bodily lumen to a stenting site. When all is ready for deployment of the stent 10, an endwise tension is applied to the pull wire 32, while the proximal end of the shaft tube 52 is restrained from endwise movement, reactive or otherwise. Endwise translation of the pull wire 32 results in proximal movement of the sheath 14. Holding the endwise position of the shaft tube 52 holds the endwise position of the pusher annulus 40 which in turn prevents any proximal movement of the stent 10 with the proximally withdrawing sheath 14.

Progressively, the sheath 14 withdraws proximally relative to the stent 10, having the effect of stretching the distal tip 16 of the sheath 14 over the radially outward surface of the stent 10, leading to progressive release and radial expansion of the stent 10, from its distal end toward its proximal end.

Note that, before there is any relative movement of the sheath 14 and pusher annulus 40, the radiologist "sees" only two marker bands, namely the first marker 40 and the radially superimposed second and third marker bands 74 and 76. However, once the sheath 14 starts to withdraw proximally, the radiologist can see the third marker, at a position proximal of the second marker. Clearly, when the third marker has moved proximally to approach, pass over, and then move proximally away from the first marker 40, one has confirmation that the stent 10 has been deployed, by full proximal withdrawal of the sheath 14.

During proximal withdrawal of the sheath 14, it will be appreciated that the proximal end 18 of the sheath 14 slides proximally over the outside surface of the shaft tube 52.

It will appreciated that there should be no endwise movement of the shaft 52 relative to its surrounding entities, whether a bodily lumen or the lumen of a guide catheter, during deployment of the stent 10. This is an opportunity for enhancement of precision of the placement of the stent, because any friction between the outside surfaces of the shaft tube 52 and the surrounding structures will only tend to confirm the location of the pusher annulus with respect to the body of the patient, and thereby the location of the stent 10 with respect to the body of the patient.

Further, the friction forces between the pull wire 32 and the luminal surfaces of the shaft tube 52 ought to be very small or minimal, as should any frictional forces between the withdrawing sheath 14 and the outside surface of the shaft tube 52, at the proximal end 18 of the sheath. Further, as the sheath 14 is relatively short in proportion to the catheter device as a whole, any friction between the outside surfaces of the sheath 14 and the surrounding bodily tissue ought also to be usefully smaller than in conventional systems where the full length of the stent deployment catheter must be moved relative to its surroundings. All of this elimination of unwanted and unhelpful friction is advantageous to the person deploying the stent, because any tactile feedback should relate more closely to events at the stent itself, and any force input at the proximal end of the device should be more completely delivered to the components around the stent 10 at the distal end of the device. There should be less lost motion in the system between the proximal and distal ends, less hysteresis, and less discrepancy between the amount of force applied at the proximal end and the amount of force delivered to the components surrounding the stent. It should be possible, with the system proposed herein, to enhance the position of stent placement, and the degree of confidence that users have when deploying stents, that the stent has been deployed smoothly and correctly.

As to design variations, the following will be evident to those skilled in the art, but so too will many more design possibilities, within the relevant published state of the art but not mentioned here.

The sheath need not include braiding. The pull wire can be threaded directly to the braiding, thereby avoiding the need for any pulling annulus between the pull wire and the sheath. Neither the distal end nor the proximal end or the sheath need be tapered. An atraumatic tip to the device can be carried on the pusher sub-system that includes the stent stopper.

Implants to be delivered by the device need not be stents and stent graft. For example, filters can be deployed with the device.

Those skilled in the art will appreciate how to build an actuator for the proximal end of the device. A suitable basis is the device described in WO 02/087470, modified to accommodate the radial inversion of the push/pull elements.

Figure 5:
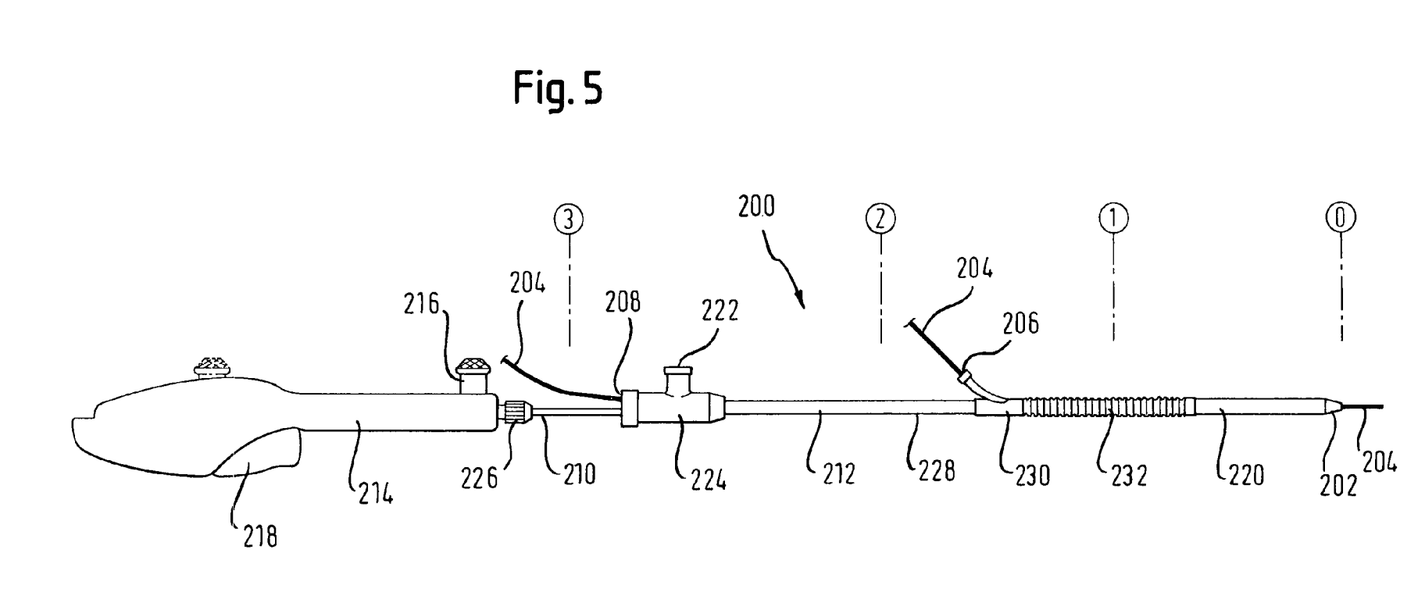
FIG. 5 is a view from the side of a catheter-based delivery system.

FIG. 5 is a general view from the side of a catheter-based delivery system 200, which, for a self-expanding stent 201, has a distal end 202 that advances over a guidewire 204, with the guidewire proximal end advancing proximally along a guidewire lumen 203 as far as a chosen one of two alternative guidewire exit ports 206, 208 both distal of the proximal end 210 of the shaft of the catheter 212 of the system. A hand unit 214 includes a first actuator 216 and second actuator 218 that can be used alternatively or sequentially to pull proximally a sheath 220 that radially overlies the self-expanding stent at the distal end of the system. At a port 222 in a proximal hub 224, flushing liquid can be introduced, to flush the system of air bubbles. A swivel nut 226 connects the catheter shaft 212 to the hand unit 214 to allow the hand unit to rotate freely around the long axis of the shaft.

Distal of the hub 224, the catheter shaft is defined by a flushing sleeve 228, which extends distally to a guider block 230 which defines the more distal of the two alternative guidewire exit ports 206. Distal of the block 230 and proximal of the stent sheath 220 is a PET bellows sleeve 232 that is contiguous with both the flushing sleeve 228 and the stent sheath 220. As the stent sheath 220 is pulled proximally, it gets closer to the adaptor 230, and the bellows sleeve 232 can undergo a reduction in length to accommodate this proximal movement. An adhesive such as DYMAX® is used to secure the bellows sleeve to the flushing sleeve.

The guidewire port is conveniently located away from both ends of the catheter system. possibly about half way along the length, or around 75 cm from the distal tip of the system.

Figure 6:
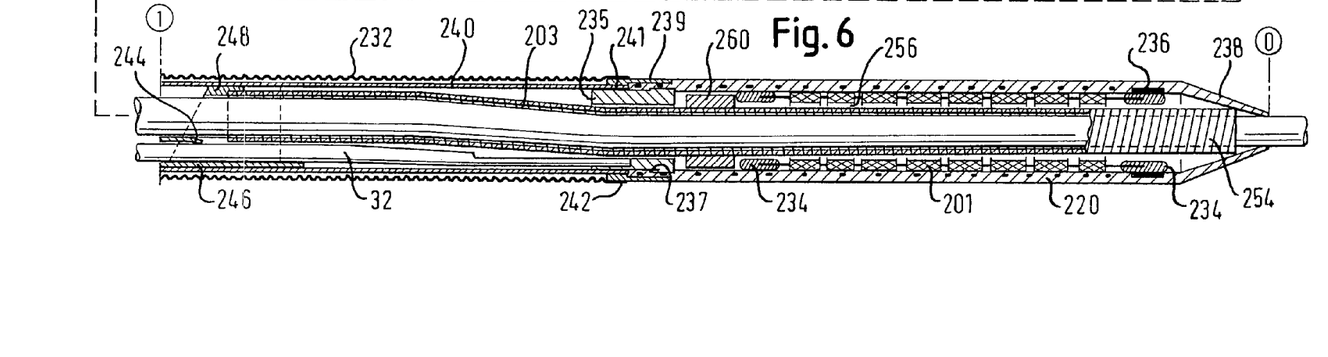
FIG. 6 is a longitudinal diametrical section through the distal end of the catheter-based delivery system of FIG. 5.

Turning to FIG. 6, we see that the stent is provided at each end with a ring of tantalum marker spoons 234 (see Applicant's WO 2002/015820). The sheath 220 confining the stent is of PEBA polymer (PEBAX®) reinforced with a braid of flat stainless steel wire at 45 or 65 pitches per inch, 0.13 or 0.075 mm wide and 0.025 mm thick and it has a liner of PTFE (TEFLON®). The sheath has a platinum/iridium marker band 236 embedded within it and overlying the distal end of the stent. Distal of the marker band is a tapered distal tip 238 made of a softer grade of PEBA. The proximal end of the sheath is surrounded by a stainless steel stepped swaged band 239 that presses the sheath 220 inwardly down over a shoulder 237 on a stainless steel pull ring 235 that is welded to the stainless steel, PTFE-coated pull wire 32. The swaged band also presses onto the pull ring the distal end 241 of a telescope tube 240, and shrunk down onto the radially outer surface of the swaged band is the distal end 242 of the bellows sleeve 232.

Figure 7:
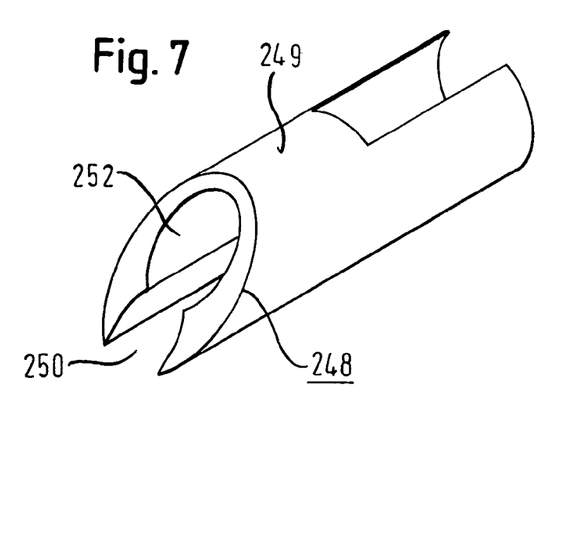
FIG. 7 is an isometric view of the adaptor block of FIG. 6

The pull wire enters the distal end 244 of a PHYNOX pusher tube 246, to which is glued (DYMAX®) a PEBA pusher adapter block 248, FIG. 7, which defines two lumens side-by-side, one (250) for the pusher tube and the other (252) for a pusher guider tube 254 which defines the guidewire lumen 203. The pusher-guider tube is made of a closed turn spiral of flat stainless steel wire 0.09 mm thick and 0.25 mm wide with a lumen diameter of 0.95 mm. The outside diameter is ground down to 1.07 mm for the section of its length that lies within the stent lumen 256. The pusher-guider tube is co-axial with the catheter shaft from the distal tip 238 of the system until the pull ring 235. Just distal of the pull ring, the spiral carries on its radially outside surface a pusher ring 260 which faces the ring 234 of spoons at the proximal end of the stent. The pusher ring can be a simple stainless steel ring, or a composite of a stainless steel ring proximally adjacent a ring of polymer such as PEEK to abut the stent. The outside diameter of the pusher ring in this embodiment is 2 mm, that is, 6 French.

Proximal of the pull ring, the pusher-guider tube veers through a gentle double bend to resume a straight line axial course parallel to the pull wire, and as far as the adapter block 248 to which it is fixed in the block lumen 252 with an adhesive (DYMAX®).

Figure 8:
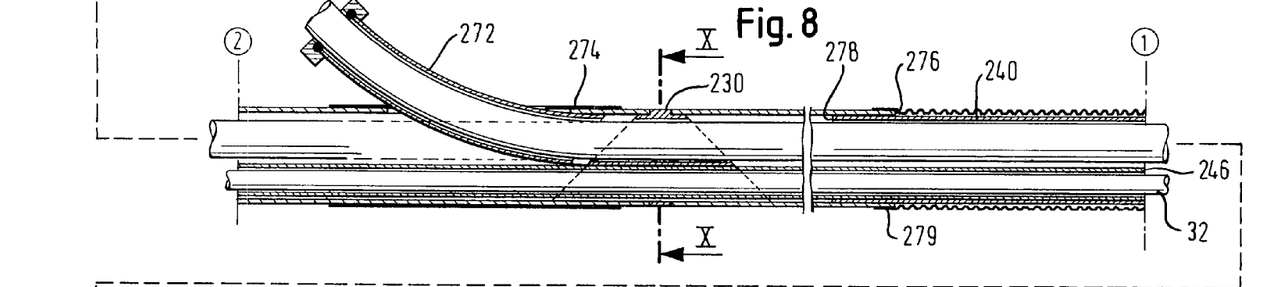
FIG. 8 is a longitudinal diametrical section through a shaft portion of the catheter-based delivery system, including a guider block
Figure 9:
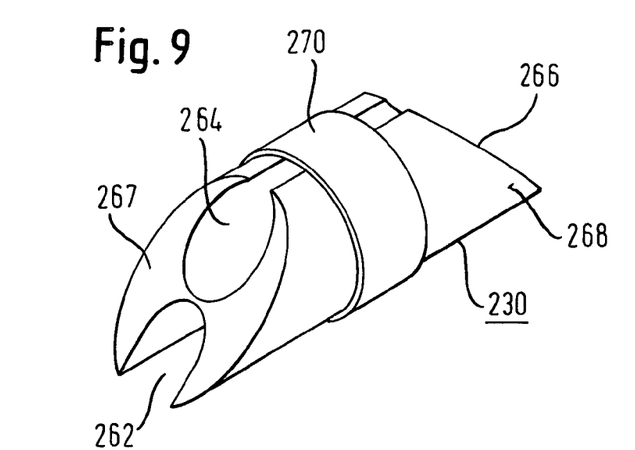
FIG. 9 is an isometric view of the guider block of FIG. 8
Figure 10:
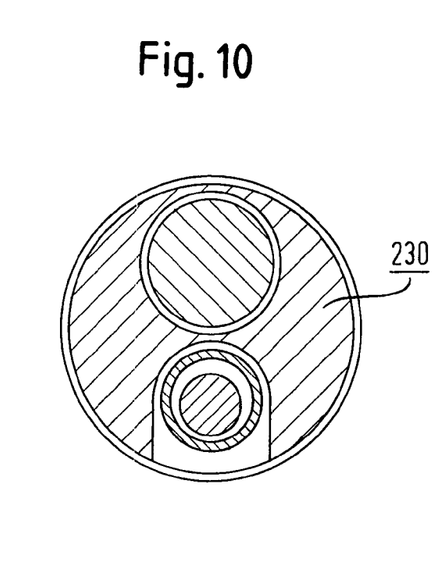
FIG. 10 is a transverse section through the guider block, on the line X-X in FIG. 8

Looking now at FIG. 8, the telescope tube 240 is of polyimide, adds stiffness to the portion of the shaft length that it occupies, and slides over the outside cylindrical surface 249 of the adapter block 248 in a proximal direction, when the stent sheath is pulled proximally to release the stent. The telescope tube in its proximal movement approaches (but does not abut) the PEBA guider block 230 that is mounted (e.g. by DYMAX® glue) to the pusher tube 246. It is located in this embodiment about 75 cm from the distal tip of the catheter. The guider block, see FIGS. 9 and 10, defines two lumens side-by-side, one (262) for the pusher tube and the other (264) for the guidewire. It has a chamfered distal face 266 that helps to steer the proximal end of the guidewire into the lumen during back-loading of the guidewire. Analogously, its proximal-facing end wall 267 is also inclined. It carries on its outside cylindrical surface 268 the flushing sleeve 228 and over that sleeve is a PEBA band 270 that squeezes the sleeve 228 onto the block surface 268, and the block material each side of lumen 262 onto the pusher tube within lumen 262. Just proximal of the block is an aperture (not visible) in the flushing sleeve 228 that receives a polyimide guidewire steering tube 272 for leading the guidewire out of its lumen in the catheter shaft at the distal exit port 206. If the user chooses not to use this exit port, the steering tube 272 is simply pulled away from the system. The side hole left behind in the wall of the flushing sleeve is closed by a thin PEBA shrink sleeve 274 that overlies radially the flushing sleeve where the steering tube exit hole is found. Absent the steering tube, the guidewire may continue to advance proximally within the flushing sleeve and alongside the pusher tube 246. The flushing sleeve has a distal end somewhat distal of the guider block 230. It receives within its distal end opening 276, telescopically, the proximal end 278 of the telescope tube 240. It is of polyimide. The bellows sleeve is glued to the flushing sleeve at an overlap 279, as mentioned above.

In a first variant, the telescope tube could be radially outside the flushing sleeve.

In a second variant, the flushing sleeve can be integral with the bellows sleeve, thereby obviating the need for any telescopic arrangement.

Figure 11:
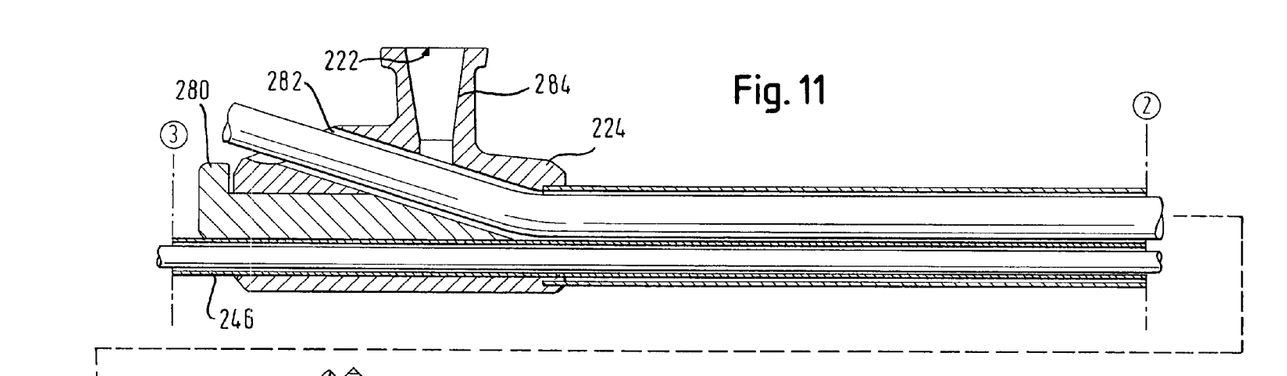
FIG. 11 is a longitudinal diametral section through the proximal part of the shaft of the catheter-based delivery system

Following proximally the shaft of the system to the more proximal of the two alternative guidewire exit ports brings us to FIG. 11 in which we see the flushing sleeve ending proximally in a polyamide hub 224 through which the pusher tube 246 continues on proximally. A stainless steel wedge piece 280 is provided in a guidewire lumen 282 of the hub to steer the proximal end of the guidewire through the hub and out of its exit port 208. Communication with the guidewire lumen and flushing sleeve lumen is the flushing port 222 with female Luer lock connector portion 284.

Figure 12:
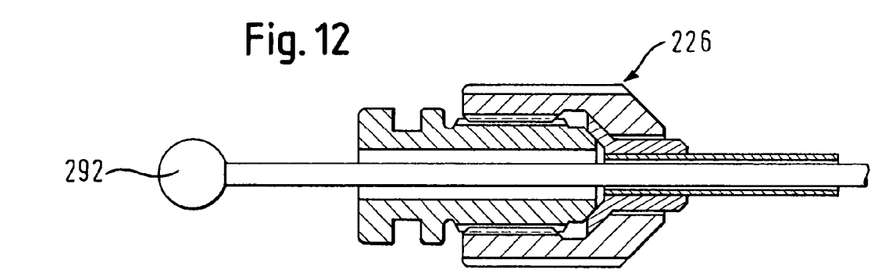
FIGS. 12 and 13 are sections through two alternative proximal ends of the pull wire of the catheter-based delivery system.
Figure 13:
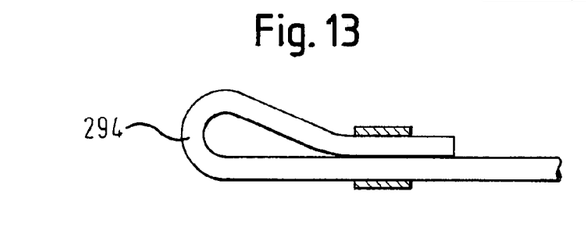
Figure 14:
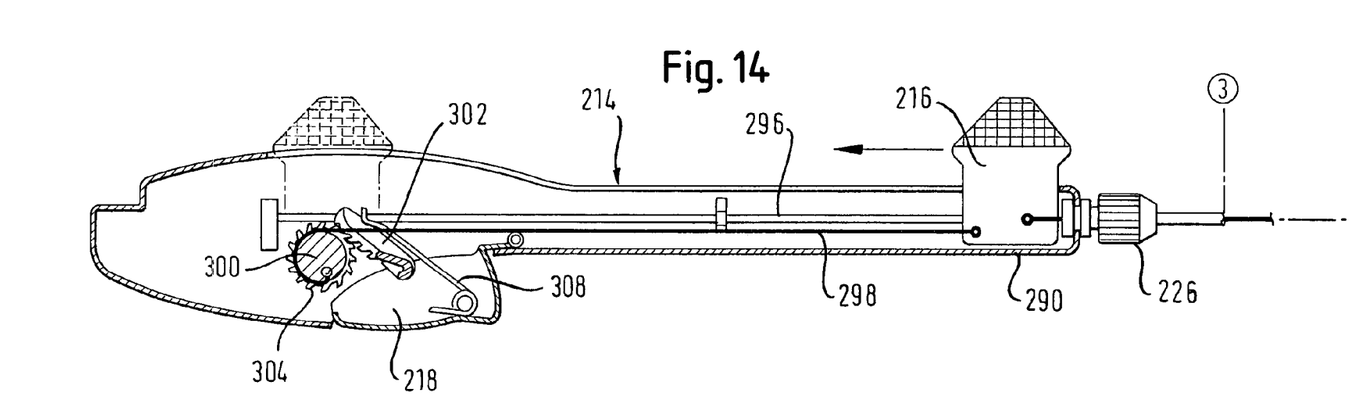
FIG. 14 is a longitudinal medial section through the hand unit of the catheter-based delivery system.

Moving on to FIGS. 12, 13 and 14, the pusher tube ends proximally in the polyamide swivel nut 226 that is mounted to the housing 290 of the hand unit 214. Thus, axial movements of the housing relative to the bodily lumen in which the delivery system lies will be transmitted from the housing to the pusher ring 260 via the push tube 246, to move the stent axially within that lumen. The pull wire is attached by a brass nipple 292 (FIG. 12) or by a loop 294 (FIG. 13) to a polyamide slider 216 (FIG. 14) which is the first actuator of the hand unit. The slider 216 runs on a pair of stainless steel rails 296 mounted to the housing, whereby pulling the slider on the rails pulls the pull wire relative to the swivel nut thereby pulling the stent sheath proximally.

But the slider 216 is on the distal end of a pulling line 298 which is wound up on a drum 300 journalled in the housing. Each pump on a trigger 218 causes a toothed rack piece 302 to advance in engagement with the teeth of a toothed wheel 304 on the drum, and a pawl stops any reverse movement of the toothed wheel and drum during return movement of the rack 302 and trigger 218 after each squeeze of the trigger. The return movement is induced by a return spring 308, the bias of which has to be overcome during each squeeze of the trigger. Thus, the stent can be released by a succession of squeezes on the trigger, or by one long smooth proximal stroke of the slider, or by any combination of these two actuators (see Applicant's earlier WO 2002/087470).

It will be appreciated that the illustrated embodiments, and the invention as claimed, make available a system to deploy a self-expanding stent, or other implant, that has a number of valuable advantages, including: i) no axial movement of the outer surface of the shaft of the delivery system relative to surrounding bodily tissue during stent deployment ii) long thin load-bearing components entirely of metal, for both co-axial parts of the stent release system, so minimizing length changes when the shaft length is suffering the endwise stresses that are imposed on it when the stent sheath is being pulled proximally off the stent iii) the tolerance of different stent lengths and diameters that flows from a design that is inherently modular (see Applicant's WO 2003/003944) iv) choice of two different lengths of guidewire lumen v) an absence of re-entrant surfaces on the tip of the system inside the stent lumen, so that withdrawal of the system after deployment of the stent should not carry the risk of dislodging or parting bodily tissue from the stenting site as the tip withdraws proximally through the stent lumen (see Applicant's WO 2001/034061).

The system illustrated in FIGS. 5 to 14 has been described with diameter dimensions. It will be appreciated that these dimensions can all be modified, more or less in proportion, to create other systems with a range of different overall diameters.

A number of published documents have been mentioned above. Many of these are from Applicant, and represent steps along the way to the present invention. It is intended that the disclosures of these earlier documents are incorporated by these references into the teaching and disclosure of the present specification.

What is claimed is:
1. A catheter having a shaft and an implant mounted on a distal end of the shaft wherein the shaft comprises:
an adapter block comprising a first shaft lumen and a second shaft lumen;
a first shaft element having a distal end within the first shaft lumen;
a second shaft element having a proximal end within the second shaft lumen;
a sheath that lies over the implant having a proximal end distal of the adapter block;

an annulus disposed outside the second shaft element and inside the sheath;
a pull wire connected to the annulus; and
a telescopic tube having a distal end connected to the proximal end of the sheath.

2. The catheter of claim 1, wherein the shaft further comprises a flushing tube connected to a proximal end of the telescopic tube.

3. The catheter of claim 2, wherein the shaft further comprises a guider block comprising a guider block lumen and a guider block guidewire lumen, wherein the guider block is disposed on the first shaft element.

4. The catheter of claim 3, wherein the second shaft element has a double bend.

5. The catheter of claim 4, wherein the first shaft element has a proximal end disposed at a handle.

6. The catheter of claim 5, wherein the annulus extends proximally of the proximal end of the sheath.

7. The catheter of claim 6, wherein the pull wire is disposed in the first shaft element.

8. The catheter of claim 7, wherein the shaft further comprises a band disposed around the flushing tube connecting the flushing tube to the guider block.

9. The catheter of claim 4, wherein a distal bend of the second shaft element is proximal of the annulus and a proximal bend of the second shaft element is distal of the adapter block.

10. The catheter of claim 9, wherein the annulus extends proximally of the proximal end of the sheath.

11. The catheter of claim 10, wherein the pull wire is disposed in the first shaft element.

12. The catheter of claim 11, wherein the shaft further comprises a band disposed around the flushing tube connecting the flushing tube to the guider block.

13. The catheter of claim 9, wherein the first shaft element has a proximal end disposed at a handle.

14. The catheter of claim 13, wherein the annulus extends proximally of the proximal end of the sheath.

15. The catheter of claim 14, wherein the pull wire is disposed in the first shaft element.

16. The catheter of claim 15, wherein the shaft further comprises a band disposed around the flushing tube connecting the flushing tube to the guider block.

17. A catheter having a shaft and an implant mounted on a distal end of the shaft wherein the shaft comprises:
an adapter block comprising a first shaft lumen and a second shaft lumen;
a first shaft element having a distal end within the first shaft lumen and a proximal end disposed at a handle;
a second shaft element having a proximal end within the second shaft lumen;
a sheath that lies over the implant having a proximal end distal of the adapter block;
an annulus disposed outside the second shaft element, disposed inside the sheath, and extending proximally of the proximal end of the sheath;
a pull wire disposed in the first shaft element and connected to the annulus;
a telescopic tube having a distal end connected to the proximal end of the sheath;
a flushing tube connected to a proximal end of the telescopic tube;
a guider block comprising a guider block lumen and a guider block guidewire lumen; and
a band disposed around the flushing tube connecting the flushing tube to the guider block, wherein:
a distal bend of the second shaft element is proximal of the annulus,
a proximal bend of the second shaft element is distal of the adapter block, and
the guider block is disposed on the first shaft element.

* * * * *